United States Patent [19]

Vanlerberghe

[11] 3,959,390

[45] May 25, 1976

[54] PROCESS OF PRODUCING MONO AND POLYHYDROXYL ETHERS

[75] Inventor: Guy Vanlerberghe, Claye-Souilly, France

[73] Assignee: L'Oreal, Paris, France

[22] Filed: July 1, 1974

[21] Appl. No.: 484,987

Related U.S. Application Data

[60] Division of Ser. No. 307,523, Nov. 17, 1972, Pat. No. 3,840,606, which is a continuation of Ser. No. 882,719, Dec. 5, 1969, abandoned.

[30] Foreign Application Priority Data

Dec. 9, 1968 Luxemburg............................ 57504

[52] U.S. Cl............................................. 260/615 R

[51] Int. Cl.$^2$.................... C07C 41/00; C07C 41/02
[58] Field of Search .................... 260/615 R, 615 B

[56] References Cited

UNITED STATES PATENTS

| | | | |
|---|---|---|---|
| 2,380,185 | 7/1945 | Marple et al.................... | 260/615 R |
| 3,840,606 | 10/1974 | Vanlerberghe.................. | 260/615 R |

*Primary Examiner*—Howard T. Mars
*Attorney, Agent, or Firm*—Cushman, Darby & Cushman

[57] ABSTRACT

Compounds having $C_2H_3(CH_2O—C(CH_3)_3)O$ groups and the process of using these compounds to produce polyhydroxyl ethers.

3 Claims, No Drawings

PROCESS OF PRODUCING MONO AND POLYHYDROXYL ETHERS

This is a division of application Ser. No. 307,523 filed Nov. 17, 1972, now U.S. Pat. No. 3,840,606 which is a continuation of Ser. No. 882,719 filed Dec. 5, 1969, now abandoned.

SUMMARY OF THE INVENTION

Polyhydroxyl monoethers and polyethers may be prepared in a known manner from lipophile compounds containing at least one reactive hydrogen atom according to a known process which comprises, as its first step, the addition or telomerization of a glycerol epihalohydrin and as its second step the substitution of the resulting polyhalogenated polyether by, e.g., an alkaline salt of carboxylic acid in a hydroxyl solvent. This process is accompanied by the formation of substantial quantities of mineral halides and is carried out at high temperatures. However, the use of this process makes it possible to avoid the disadvantages inherent in the reactivity of the hydroxyl group of glycidol.

There are other known processes in which epoxides having trialkyl-siloxy or triaryl-siloxy groups are used to prepare polyethers having hydroxyl groups which are statistically distributed with respect to the molecules produced. This process consists, in the first step, in polymerizing or copolymerizing trialkyl or triarylsilyl glycidyl ethers with anionic catalysts, and then, in a second step, reconstituting the hydroxyl group by hydrolysis. These silicated epoxides have the disadvantage of being difficult to make and their behavior in telomerization reactions is not known.

It is the purpose of the present invention to avoid the difficulty encountered in the course of the preparation of polyhydroxyl polyethers using the processes heretofore known.

It is accordingly the object of the present invention to provide a process of preparing polyhydroxyl ethers and polyethers using tertio-butyl-glycidyl ether as a starting point, that is to say using an ether in which the hydroxyl group of the glycidyl is protected by replacing the hydrogen atom by a tertio-butyl radical as a substituent on the oxygen during a first reaction, the tertio-butoxy group then catalytically is split off the oxygen atom and replaced by a hydrogen atom to produce the hydroxyl group again.

It is a further object of the present invention to provide the new chemical products consisting of the telomerization products of tertio-butyl-glycidyl ether which may be derived from mono- or polyfunctional compounds belonging to the class consisting of alcohols, thiols and phenols.

It has been discovered that it is possible to prepare in a first step, using an addition reaction or addition and polymerization reaction, monoethers or polyethers containing one or more oxyalkylene constituents having the general formula:

$$\left\{ C_2H_3 (CH_2O-C(CH_3)_3) O \right\} \quad (I)$$

which correspond to the developed formulas of the two isomeric radicals:

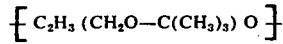
 and 
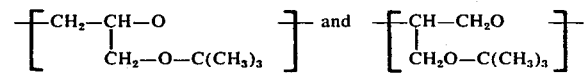

and then decompose or heterolyze these compounds in the second step by a catalytic process in order to produce polyhydroxyl ethers and polyethers.

In the first step the tertio-butyl-glycidyl ether is reacted, in the presence of a catalyst, with a compound containing at least one reactive hydrogen atom and having the general formula:

$$R (XH)_a \quad (II)$$

in which R is a radical having a valence equal to $a$ as hereinafter defined and which is selected from the group consisting of a hydrogen atom; a hydrocarbon radical, a substituted hydrocarbon which may contain one or more hetero-atom such as O, N, S, in which said hydrocarbon is a saturated or unsaturated aliphatic residue or alkyl or alkenyl group having a linear or branch chain and containing 1 to 30 carbon atoms, which may carry one or more halogen atoms, a polyoxyalkylene radical, an alkyl polyoxyalkylene radical or an alkenylpolyoxyalkylene radical containing 3 to 60 carbon atoms and 1 to 10 oxygen atoms; or a saturated or unsaturated cyclo-aliphatic group containing 6 to 30 carbon atoms and which may also carry substituent groups such as alkyl, alkylene, halogen, or an aromatic substituted or unsubstituted radical such as phenyl, naphalkylphenyl, alkylene phenyl, etc., X represents identical or different hetero atoms which may be oxygen or sulfur; $a$ represents a whole number between 1 and 6 and preferably between 1 and 3 inclusive. Among the compounds responding to the general formula R (XH)$_a$, are:

1. monoalcohols such as:

the lower alkanols comprising up to 7 carbon atoms such as methanol, ethanol, 1-propanol, 2-propanol, 1-butanol, isobutanol, tertiary butyl alcohol, 2-methyl-1-butanol, 3-methyl-1-butanol, 1-hexanol, allyl alcohol;

the fatty alcohols comprising 8–22 carbon atoms such as the saturated linear chain, fatty alcohols such as 1-octanol, 1-decanol, 1-dodecanol, 1-tridecanol, 1-tetra decanol, 1-hexadecanol, 1-octadecanol, 1-cicosanol, 1docosanol;

the saturated branched chain fatty alcohols such as 1-hexanol, 2-ethyl, decoctanol, 2-methyl-1-decanol, 2-methyl-1-dodecanol, 2-methyl-1-tridecanol, 2-methyl-1-tetradecancol, 1-tetradecanol, 2,3,5,7-tetramethyl-1-nonanol, 2,4,7 trimethyl-1-nonanol, 2-hexyl-1-decanol, 2-octyl-1-dodecanol;

the unsaturated fatty alcohols such as oleic alcohol, elaidic alcohol, and erucylic alcohol;

the waxy alcohols such as carylic alcohol and melissic alcohol;

the alcohols of the alicyclic series such as cyclohexanol, methylcyclohexanol, cholesterol, cholestanol, lanosterol, dihydrolanosterol, abietinol; etc.

2. polyols such as ethylene glycol, diethylene glycol, triethylene glycol, propylene glycol, dipropylene glycol, 1,3-propanediol, butylene glycol, glycerol, long chain diols such as 1,2-decanediol, 1,2-dodecanediol, 1,2-tetradecanediol, 1,2-hexadecanediol, and 1,2-octadecanediol;

3. halogenated alcohols such as monoglycolhydrin; 2-chloro-1-ethanol, 1-chloro-2-propanol, glycerol 1' α-monochlorohydrin; 3-chloro-1,2-propane diol, the glycerol dihydrochlorins such as 1,3-dichloro-2-propanol and 2,3-dichloro-1-propanol;

4. water;
5. thiols and polythiols such as methyl mercaptan, dodecyl mercaptan, tetradecyl mercaptan, octadecyl mercaptan, ethane dithiol;
6. the mercapto alkanols or mercapto polyols such as 2-mercapto-1-ethanol, 1-mercapto-2-propanol, 3-mercapto-1,2-propanediol;
7. phenolic compounds such as phenol, cresol, p-octyl-phenol, p-iso-nonyl-phenyl, p-tertio-dodecyl-phenol, p-iso-dodecyl-phenol.

The hydroxyl compounds used as starting compounds are generally used in the pure state. In the case of fatty alcohols and waxy alcohols, however, they are most often used in the form of isomeric mixtures and homologous derivatives obtained from animal or vegetable oils or fats such as copra, tallow, etc. or tall-oil and lanolin and like products. These compounds may also be prepared by synthesis as is the case, for example, with the alcohols prepared according to the "Alfol" process or the "Oxo" process, by the Guerbet reaction, from modified fatty acids according to the process described in U.S. Pat. No. 2,812,342, from cyclic fatty acids, or even by oxidation of parafins or by hydration of α-olefins.

The catalysts used in conducting the reaction of tertio-butyl-glycidyl ether and compounds responding to the formula $R(XH)_a$ may be basic catalysts or acid catalysts.

The basic catalyst may be selected for example, from among alkali metals, Li, Na, K, etc. and their hydroxides, their alcoholates, or their mercaptides, in the ratio of 0.1 to 1% of the weight of the reaction mass.

It is also possible to use tertiary amines, such as, for example, triethylamine, in a ratio of 0.1 to 5% and preferably 1 to 5% by weight, and also pyridine, N,N'-tetramethyl-diamino-1,3-butane and N,N'-tetramethyl-diamino-1,2-ethane.

As acid catalysts, which are preferably used in the presence of alcohol, the following are suitable: Lewis acids such as $BF_3$, $SnCl_4$, $SbCl_5$, in the proportion of 0.1 to 1% by weight of the total reaction mass.

The reaction takes place at a temperature of 80° to 180°C when basic catalysts are used, and at a temperature below 120°C when acid catalysts are used. If boron fluoride is used, the reaction preferably takes place at temperatures below 100°C.

The proportion $n$ between the tertio-butyl-glycidyl-ether and the compound responding to formula $R(XH)_a$, expressed in moles of epoxides per gram atom of reactive hydrogen varies from 0.1 to 10 depending on the starting products used and the compound which is to be obtained at the end of the first step. When alcohols are used as the starting compounds and it is desired to avoid the formation of polymers, this proportion should be less than 1.

When the compound $R(XH)_a$ contains hydrogen atoms which are more mobile than those present in alcohols, as for example, in the case of thiols and phenols, it is possible by selecting the value of this ratio close to 1 and using an alkaline catalyst to prepare monoaddition products with a good yield. These may be isolated by distillation or crystallization.

In most cases telomerization reactions are obtained when an epoxide is reacted with a compound containing an active hydrogen atom, for example when $a$ equals 1. The reaction then takes place as follows:

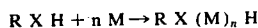

with M representing the molecule of an epoxide monomer and n the degree of polymerization. The compound RHS is then called "telogene", the compound M "taxogene", and the reaction product $RX(M)_nH$ is called a "telomer". In the present case M represents tertio-butyl-glycidyl ether, but it is obvious that it is also possible to utilize tertio-butyl-ethers of epoxide alcohols which are homologs of glycidol.

Applicant has discovered that the tertio-butoxy group is resistant to a catalysized telomerization reaction. That is to say, this reaction takes place without scission of the ether bond and without forming undesirable products even when carried out in the presence of boron fluoride, which is completely unexpected. In effect, it is known that the tertio-butoxy group is unstable in an acid medium and it would be expected that telomerization or polymerization in the presence of acid catalysts, and especially of boron fluoride would be difficult to carry out and produce degradation products. It is thus very remarkable that these reactions take place, on the contrary, under excellent conditions, as indicated, in particular with respect to the small degree of coloration of the telomerization products obtained. In most cases these products are either colorless or have only the color of the starting products used.

In the absence of secondary reactions, the average degree of polymerization $n$ is equal to the statistical average number of epoxide molecules participating in the reaction per —XH group. This number $n$ may thus be a decimal number, it being understood that the degree of polymerization "N" corresponding to a given molecule of the mixture may obviously be greater than $n$. While it is difficult to determine the upper limit of N, this limit may be estimated at 2 to 3 times $n$.

In the preferred method the catalyst is mixed with the compound $R(XH)_a$. The mixture is then heated to the selected optimum reaction temperature depending on the compound being used. The tertio-butyl glycidyl-ether is then added, little by little, while stirring.

As a general rule, the reaction is carried out without a solvent, but a solvent may be used if it is inert with respect to the epoxides being used. The completion of telomerization is indicated by the disappearance of epoxide groups in the reaction mixture.

The second step of the process consists in splitting off the tertio-butoxy group or groups attached to the oxyalkylene groups so as to replace these groups with hydrogen to form hydroxyl radicals.

This reaction is carried out in the presence of water and a catalyst such as a sulfonic acid containing compound or compounds. In order to split off the tertio-butoxy group, paratoluene sulfonic acid has heretofore been used in at least equimolecular quantities.

Applicant has now discovered the unexpected fact that the same result may be obtained by using the sulfonic acids in catalytic quantities, which constitutes a considerable advantage with respect to the splitting process, the separation of the final product, the degree of purity of this product, and, in certain cases, the possibility of using the reaction product directly in the state in which it is produced.

The catalysts used in the second step of the present invention may be classified in two groups corresponding to the aromatic and aliphatic sulfonic acids.

Among the aromatic sulfonic acids are benzene sulfonic acid, paratoluene sulfonic acid, and sulfosalicylic acid. Among the aliphatic sulfonic acids, and preferably those which include as substituents hydroxyl or carboxyl groups, are: hydroxyalkane sulfonic acids such as 3-hydroxy propane sulfonic acid, the sulfonation products of α-olefins containing 8 to 18 carbon atoms, the sulfocarboxylic acids and their esters, and in particular the α-sulfonated carboxylic acids such as sulfo-acetic acid, α-sulfolauric acid, α-sulfo palmitic acid, and α-sulfo stearic acid, as well as the esters of these acids and lower alcohols containing 1 to 4 carbon atoms.

The sulfo-carboxylic acides and their esters have been shown to be, in a completely unexpected way, especially valuable as catalysts. These catalysts are used in proportions of about 0.5 to 20% by weight, but preferably less than 10% and most frequently 0.5 to 5% by weight of the polyethers used as starting materials. These proportions are calculated on the basis of the pure anhydrous catalysts. In order to split or heterolyze the tertio-butoxy group, water is used in a proportion of 10 to 200% by weight of the polyethers, depending upon the number of tertio-butoxy groups in their molecule. The more tertio-butoxy groups, the more water should be used.

The reaction is carried out at a temperature of 50°–120°C and preferably at a temperature of about 90° to 100°C.

In a preferred method of carrying out the invention, the polyether is heated while stirring and the catalyst is then introduced, after which the water is progressively added.

It follows that the water participates in the reaction to the extent that it is introduced. It is important that the catalyst always be present in a sufficient degree of concentration. It should also be noted that it is important not to introduce the catalyst or a mixture of catalysts in the form of a dilute aqueous solution because the tertio butyl replacement reaction does not then take place under satisfactory conditions in the case of a too strong dilution. However, it is not necessary to use only anhydrous catalysts and crystallized hydrates for aqueous solutions containing as much as 50% or more by weight of these catalysts may be advantageously used.

The products resulting from the heterolysis reaction may be soluble or insoluble in water but in the latter case they usually disolve in the water in substantial quantities and it follows that the reaction mixture is generally homogeneous. The heterolysis may also be carried out in a hydroalcoholic medium, for example in mixtures of water and ethanol or water and tertiary butyl alcohol or some other low molecular weight alcohol.

At the end of the second step reaction the catlayst or mixture of catalysts is eliminated either by precipating it in the form of insoluble salts, followed by filtration, or by passing the reaction mixture through a basic ionic exchange resin, or simply by neutralization with a suitable organic or mineral base. When the catalysts as well as the reaction product contains a hydrocarbon chain having at least 8 carbon atoms, it is advantageous to neutralize it with an alkaline base. This produces, in addition to the polyhydroxyl polyether which constitutes a non-ionic surface active agent, an additional anionic hydro-soluble surface active agent, this agent may be retained in the final mixture for use in numerous applications in which it is directly useful.

When the catalyst used is a sulfocarboxylic acid, the polyhydroxyl polyethers formed during heterolysis may be partially esterified without adversely affecting the completion of this reaction. At the end of this reaction these sulfocarboxylic acid esters and polyhydroxyl polyethers may be saponified in the usual manner.

The following representative examples illustrate the preparation of glycerol or polyglycerol monoalkyl ethers in order that the object of the present invention may be better understood:

EXAMPLE 1

Preparation of glycerol n-hexyl ether:

4.7g of a solution containing 22.7% sodium methylate in methanol is added to 61.2g of dehydrated n-hexanol. The methanol is eliminated by heating the mixture to 155°C. After cooling the mixture to 130°C, 39g of tertio-butyl-glycidyl-ether is introduced gradually over a two hour and 50 minute period. This ether has a boiling point of 87°–88°C under 88 mm of mercury and a purity of 95% as determined by measurement of the epoxide function. The secondary products which it contains are chlorinate derivatives having a chlorine content of 0.58%. The reaction is completed by heating the mixture at reflux for one hour.

The tertio-butoxy-hexyl-oxypropanol produced is isolated by fractional distillation. The glycerol diether is collected at 143°–147°C under a pressure of 17 mm of mercury. The glycerol diether is then used to prepare glycerol n-hexyl ether in the following manner:

950 mg of paratoluene sulfonic acid is added to 19g of the glycerol diether. The mixture is heated in a water bath and water is introduced thereinto at a rate such that this water is progressively solubilized. In this way 44 ml of water is added in two hours and 15 minutes while maintaining a single phase in the mixture. By diluting it with an excess of about 14 ml of water, the mixture is separated into two phases. The aqueous layer is decanted after neutralizing the catalyst with a 40% sodium hydroxide washing solution and the organic phase is washed with an equal weight of water.

The crude product is separated by decantation and subjected to fractional distillation.

This yields 11g of glycerol n-hexyl ether having a boiling point of 150°C under 15 mm of mercury.

EXAMPLE 2

A. Reaction of tertio-butyl-glycidyl-ether with lauric alcohol (telomerization):

0.45 ml of an acetic complex of boron fluoride containing 36% $BF_3$ is added to 46.5 g (0.25 mol) of 1-dodecanol.

The mixture is heated to 70°C and 130 g of tertio-butyl-glycidyl ether is added over a one hour and 30 minute period. The number of epoxide groups in this ether was 97.5% of the theoretical quantity.

The temperature is kept at 70°–80°C during the introduction of the epoxide. The operation is completed by heating the reaction mixture in the water bath for half an hour. The telomerization product thus obtained is a colorless oil having the formula:

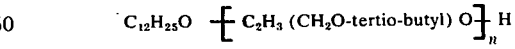

in which $n$ has a statistical average value of 4.

B. Heterolysis:

3 g of paratoluene sulfonic acid is added to 60g of the telomer obtained in step A. The mixture is heated to 90°C and water is added at a rate such that the mixture remains homogeneous. 20 ml of water is thus added over a one hour and 20 minute period.

The temperature of the reaction mixture is then maintained at 90°–95°C for two hours while evaporating the tertio-butyl alcohol formed during the course of the reaction.

202 g of the resulting product is collected and dried in a vacuum drier. The yield is 192 g of a translucent paste which is soluble in water and consists of a mixture of compounds having the formula:

$$C_{12}H_{25}O \left[ C_2H_3 (CH_2OH) O \right]_n H$$

in which $n$ has a statistical average value of 4.

EXAMPLES 3–7

Starting with a telomer of tertio-butyl-glycidyl-ether, or T.B.G.E., which is identical to the one in Example 2, a polyhydroxyl polyether having the above formula is prepared under the conditions summarized in the following table in which the percentages by weight of the anhydrous catalyst and water are expressed in proportion to the mass of the T.B.G.E. telomer used in the process, the reaction times indicated being the times required to produce a product which is soluble in water.

| EXAMPLE No. | CATALYST Substance | Percentage | Water | Temperature of reaction | Time of reaction |
|---|---|---|---|---|---|
| 3 | 5-sulfo-salicylic acid | 6.3% | 56.6% | 90–95°C | 2hr,15min |
| 4 | 5-sulfo-salicylic acid | 3.15% | 56.6% | 90–100°C | 2hr,30min |
| 5 | 5-sulfo-salicylic acid | 1.57% | 113% | 100–110°C | 6 hours |
| 6 | α-sulfo-stearic acid | 10.5% | 75% | 90–100°C | 1hr,25min |
| 7 | α-sulfo-acetic acid | 0.8% | 94% | 95–100°C | 1hr, 5min |

EXAMPLE 8

As in Examples 2–7, a telomer is used which results from the reaction of 4 mols of tertio-butyl-glycidyl ether with 1 mol of dodecanol.

· A solution of 3 hydroxy-propane-1-sulfonic acid is also prepared by hydrolyzing 12.2 g of propane sulfone while hot with 16 g of water.

2.4 g of this solution and 5 ml of water is then added to 30 g of poly-tertio-butyl-glycidyl-ether.

40 ml of ethyl alcohol at 96°C is then introduced into the remaining heterogeneous mixture after an hour of heating, the heterogeneous mixture so as to obtain a single phase.

After heating at reflux for seven hours the ethyl alcohol is evaporated over a period of five and ½ hours and the reaction mixture is then kept at 90°–100°C for another five hours. The product obtained in this way is soluble in water. After dehydration, it takes the form of a paste consisting of a mixture of compounds similar to those described in Examples 2–7.

EXAMPLE 9

A. Reaction of tertio-butyl-glycidyl ether with a mixture of cetyl and stearyl alcohols:

The mixture of fatty alcohols used as a starting material consists of cetyl alcohol and stearyl alcohol in substantially equal proportions. This mixture has the following characteristics:

| -Hydroxyl number | 211 |
| -Iodine number | 0.5 |
| -Melting point | 52.5°C |

0.33 ml of an acetic complex of boron fluoride containing 36% $BF_3$ is added to 66.6 g of this mixture, which has first been melted.

The temperature is then kept at 70°–80°C and 65 g of tertio-butyl-glycidyl ether is introduced into the reaction mixture over a period of 20 minutes.

This results in a telomerization product which no longer contains an epoxide and is in the form of a colorless oil.

B. Heterolysis:

0.53 g of sulfo-acetic acid having an $HO_3$—S—$CH_2$—COOH content of 80.5% is added to 52.6 g of the telomer obtained in step A.

The mixture is heated to 100°C for 20 minutes. Water is then added little by little so as to maintain a homogeneous mixture, while keeping the temperature of the mixture at 100°C. Under these conditions 4.5 ml of water is added over a 3 hour and 20 minute period.

The product obtained after vacuum drying has the following characteristics:

| -Acid number | 6.1 |
| -Hydroxyl number | 370 |

These properties remain substantially the same when the reaction is prolonged for another 4 hours.

EXAMPLE 10

A. Preparation of a telomer having the following formula:

$$C_{18}H_{37}O \left[ C_2H_3 (CH_3) O \right]_{n'} \left[ C_2H_3 (CH_2O\text{-tertio-butyl}) O \right]_n H$$

in which $n'$ has a statistical average value of about 5 and $n$ has a statistical average value of 2.

0.9 ml of an acetic complex of boron fluoride containing 36% $BF_3$ is added to 57.5 g of stearyl alcohol of an industrial grade which has been vacuum-dried and melted.

61 g of propylene oxide is added to this mixture in 40 minutes, while maintaining the temperature at 75°–85°C.

This produces a stearyl polyoxypropylene alcohol. 0.2 ml of an acetic complex of boron fluoride is added to 59 g of the compound and this is reacted with 26 g of tertio-butyl-glycidyl ether at a temperature of 75°–80°C. This operation takes 25 minutes and yields a liquid polyether.

B. Heterolysis.

425 mg of sulfo-acetic acid containing 80.5% of HO$_3$S—CH$_2$COOH is added to 42.5 of the product obtained in step A.

The procedure is the same as in the previous examples and 7 ml of water is introduced into the reaction mixture over a period of 4 and ½ hours, the temperature being 100°C.

The result is a polyhydroxyl polyether having the formula:

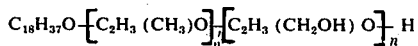

in which $n'$ and $n$ have the statistical average values of 5 and 2 respectively.

This product is purified by washing in water after neutralization of the catalyst with an aqueous solution containing 40% of sodium hydroxide.

The product is dried and in dry form it is a semisolid having a final melting point of 32°C.

EXAMPLE 11

Preparation of 3-phenoxy 1,2-propanediol:

A. Reaction of phenol with tertio-butyl-glycidyl ether 5.35 g of a solution containing 24.4% of sodium methylate in methanol is added to 47 g of melted phenol. The methanol is eliminated by evaporation and 63 g of tertio-butyl-glycidyl ether is then introduced into the mixture of phenol and catalyst.

Measurement of the epoxides show that 96% of them have reacted after 2 hours and 35 minutes of reaction at 90°–100°C.

The reaction mixture is washed with water after the alkaline catalyst has been neutralized with hydrochloric acid, and the mixture is then dried.

This yields 98 g of the product, which is then subjected to fractional distillation.

This separates out a compound having a boiling point of from 113 to 115°C under a pressure of about 0.1 mm of mercury. This product has a hydroxyl index corresponding to the value calculated for the tertio-butyl ether of phenoxy-propanediol.

B. Heterolysis:

0.6 g of sulfo-acetic acid is added to 60.5 g of terbutylic ether of phenoxy propanediol.

10 ml of water is introduced into the reaction mixture in an hour and 30 minutes.

After 4 and ½ hours of reaction at 100°–105°C, evaporation yields 44.5 g of a product which is partially esterified with sulfo-acetic acid. This product is treated with caustic potash which has been purified by solution in alcohol in a boiling water bath so as to form the dipotassium salt of sulfoacetic acid. This salt is precipitated in an alcohol medium. It is easily separated by filtration and the alcohol is evaporated. Fractional distillation yields 39.5 g of phenoxy propanediol, the boiling point of which under 0.05 mm of mercury is 115°C.

EXAMPLE 12

Preparation of dodecyl-thio-propanediol:

A. Reaction of dodecyl mercaptan with tertio-butyl-glycidyl ether.

39 g of tertio-butyl-glycidyl ether is added over 45 minutes to 61.5 g of dodecyl mercaptan, in the presence of 0.5 ml of triethylamine as a catalyst, and at a temperature of 90°–95°C.

The temperature of the reaction mixture is then increased to 120°–130°C. At the end of 2 hours of reaction at this temperature 63% of the thiol has been consumed.

After a new addition of 0.5 ml of triethylamine and extended heating at 120°–130°C for 2 hours, the percentage of transformation increased to 78%.

The crude product obtained in this manner is washed once with 100 ml of an 0.06 N aqueous solution of hydrochloric acid, and then twice with 100 ml of water.

After vacuum drying in a water bath the yield is 87.5 g of a yellow liquid which solidifies when cooled.

Vacuum distillation yields 60.4 g of a compound having a boiling point under a pressure of 0.5 mm of mercury of 170°–176°. This compound is in the form of a colorless liquid.

B. Heterolysis:

0.43 g of sulfo-acetic acid having a HO$_3$S—CH$_2$COOH content of 80.5% is added to 43 g of the tertio-butyl ether of dodecyl-thio-propanediol.

The mixture is heated in a water bath and 4 ml of water is progressively introduced over a period of 3 and ½ hours.

The reaction mixture is then vacuum-dried while hot. The yield is 36 g of the crude product which is treated with concentrated sodium hydroxide in order to transform the catalyst into its disodium salt. This product is then washed twice with 100 ml of water.

After drying the result is 33.5 g of a waxy product which melts at about 36°C.

Starting from this point, two successive recrystallizations in ligroin or petroleum ether the result is a 35% yield of dodecyl-thiol-propanediol, which is 98.5% pure when evaluated in terms of its hydroxyl index.

EXAMPLE 13

Preparation of a polyglycerol chloride:

A. Reaction of glycerol monochlorohydrin (3-chloro-1,2-propanediol) with tertio-butyl-glycidyl ether:

0.25 ml of an acetic complex of boron fluoride containing 36% BF$_3$ is added to 22.1 g of glycerol monochlorohydrin.

The mixture is heated to 70°C and 78 g of tertio-butyl-glycidyl ether is introduced drop by drop, while keeping the temperature at 65°–70°C.

The reaction is exothermic until the addition of epoxide has been completed.

The resulting product is a viscous liquid, almost colorless. It contains no epoxide.

The amount of hydroxyl groups is 4.2 milligram equivalents.

The theoretical value calculated for the compound responding to the formula:

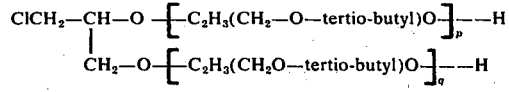

in which the sum $(p + q)$ has a statistical average value of 3, and corresponds to 4 milligram equivalents.

B. Heterolysis:

0.5 g of sulfo-acetic acid having a HO$_3$S — CH$_2$COOH content of 80.5% is added to 50 g of the product obtained in step A.

After heating for 20 minutes at 90°–95°C, 8 ml of water is added to the mixture over a period of 2 hours and 30 minutes while keeping the temperature at about 100°C. It is then stirred for an additional 2 hours at this temperature.

The crude product obtained in this manner is vacuum dried and subjected to two extractions with ligroin (50 ml each time).

It is then redissolved in 100 ml of isopropanol and the catalyst neutralized with 40% aqueous sodium hydroxide.

The alcoholic solution is decolored or clarified with animal black and then filtered.

After evaporation of the alcohol, the yield is 25 g of a very viscous light brown product which is soluble in water and has the following analytical characteristics:

| Chlorine | 2.9 milligram equivalents |
|---|---|
| Hydroxyl | 15.7 milligram equivalents |

The theoretical values calculated for the compound represented by the formula:

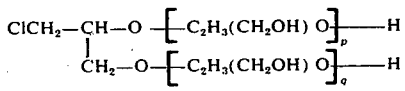

in which the sum $(p + q)$ has a statistical average value of 3 are as follows:

| Chlorine | 3 milligram equivalents |
|---|---|
| Hydroxyl | 15 milligram equivalents |

It is eventually possible to obtain the tertiary butyl intermediates by a fractionnary distillation, and particularly under high vacuum conditions.

The splitting off reaction which constitue the second step of the process, produces well defined polyhydroxylated derivatives, which could be used as surface active agents in pharmaceutics and in food products.

The novelty of the process reside essentially in the fact that it is now possible to obtain with a good degree of purity, products which are directs precursors of polyhydroxylated active surface agents, and to prepare afterwards these agents, by the beforesaid splitting off process.

What is claimed is:

1. A process for preparing a member selected from the group consisting of polyhydroxyl ether and polyhydroxyl polyether consisting essentially of
    a. heating at a temperature between 50°–120°C a corresponding ether selected from the group consisting of monoether and polyether, containing at least one oxyalkylene radical having the formula selected from the group consisting of

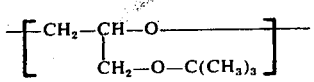

and

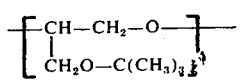

said corresponding ether being produced by reacting tertiobutyl glycidyl ether and a compound of the formula $R(XH)_a$ wherein $a$ is an integer of 1–6, R is an aliphatic hydrocarbon having 1–30 carbon atoms, saturated or unsaturated, linear or branched and carrying 1–2 chloro substituents and X is O, the proportion of said tertiobutyl glycidyl ether to said compound expressed in moles of epoxide per gram atom of reactive hydrogen being 0.1 – 10, at a temperature of 80° – 180°C in the presence of a basic catalyst selected from the group consisting of alkali metal and the hydroxide, alcoholate and mercaptide thereof, present in amounts of 0.1 – 1 percent by weight of the reaction mass, the heating of said corresponding ether being carried out in the presence of a catalyst selected from the group consisting of benzene sulfonic acid, paratoluene sulfonic acid, sulfosalicylic acid, 3-hydroxy propane sulfonic acid, sulfoacetic acid, α-sulfolauric acid, α-sulfopalmitic acid and α-sulfostearic acid, said catalyst being present in amounts of about 0.5 – 20 percent by weight of said corresponding ether; and
    b. progressively adding water to said corresponding ether and said catalyst being heated, in amounts of 10 – 200 percent by weight of said corresponding ether.

2. A process for preparing a member selected from the group consisting of polyhydroxyl ether and polyhydroxyl polyether consisting essentially of
    a. heating at a temperature between 50°– 120°C a corresponding ether selected from the group consisting of monoether and polyether, containing at least one oxyalkylene radical having a formula selected from the group consisting of

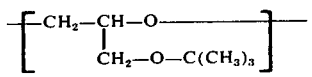

and

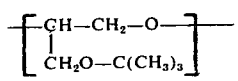

said corresponding ether being produced by reacting tertiobutyl glycidyl ether and a compound of the formula $R(XH)_a$ wherein $a$ is an integer of 1–6, R is an aliphatic hydrocarbon having 1–30 carbon atoms, saturated or unsaturated, linear or branched and carrying 1–2 chloro substituents and X is O, the proportion of said tertiobutyl glycidyl ether to said compound expressed in moles of epoxide per gram atom of reactive hydrogen being 0.1 – 10, at a temperature of 80° – 180°C in the presence of a tertiary amine catalyst selected from the group consisting of triethylamine, pyridine, N,N'-tetramethyl-1,3-diamino butane and N,N'-tetramethyl-1,2-diamino ethane present in amounts of 0.1 – 5 percent by weight of the reaction mass, the heating of said corresponding ether being carried out in the presence of a catalyst selected from the group consisting of benzene sulfonic acid, paratoluene sulfonic acid, sulfosalicylic acid, 3-hydroxy propane sulfonic acid, sulfoacetic acid, α-sulfolauric acid, α-sulfopalmitic acid and α-sulfostearic acid, said catalyst being present in amounts of about 0.5 – 20 percent by weight of said corresponding ether; and
    b. progressively adding water to said corresponding ether and said catalyst being heated, in amount of 10 – 200 percent by weight of said corresponding ether.

3. A process for preparing a member selected from the group consisting of polyhydroxyl ether and polyhydroxyl polyether consisting essentially of
a. heating at a temperature between 50°–120°C a corresponding ether selected from the group consisting of monoether and polyether, containing at least one oxyalkylene radical having the formula selected from the group consisting of

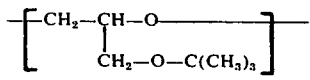

and

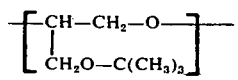

said corresponding ether being produced by reacting tertiobutyl glycidyl ether and a compound of the formula $R(XH)_a$ wherein $a$ is an integer of 1–6, R is an aliphatic hydrocarbon having 1–30 carbon atoms, saturated or unsaturated, linear or branched and carrying 1–2 chloro substituents, and X is O, the proportion of said tertiobutyl glycidyl ether to said compound expressed in moles of epoxide per gram atom of reactive hydrogen being 0.1 – 10, at a temperature below 120°C in the presence of a Lewis acid catalyst present in amounts of 0.1 – 1 percent by weight of the reaction mass, the heating of said corresponding ether being carried out in the presence of a catalyst selected from the group consisting of benzene sulfonic acid, paratoluene sulfonic acid, sulfosalicylic acid, 3-hydroxy propane sulfonic acid, sulfoacetic acid, α-sulfolauric acid, α-sulfopalmitic acid and α-sulfostearic acid, said catalyst being present in amounts of about 0.5 – 20 percent by weight of said corresponding ether; and
b. progressively adding to said corresponding ether and said catalyst being heated, in amounts of 10 – 200 percent by weight of said corresponding ether.

* * * * *